(12) United States Patent
Cheema et al.

(10) Patent No.: US 8,348,981 B2
(45) Date of Patent: Jan. 8, 2013

(54) MINIMAL ACCESS OCCIPITAL PLATE

(75) Inventors: Naveed Cheema, Breinigsville, PA (US); Ron Apfelbaum, Salt Lake City, UT (US); Fred Geisler, Aurora, IL (US); Larry Khoo, Studio City, CA (US)

(73) Assignee: Aesculap Implany Systems, LLC, Center Valley, PA (US)

( * ) Notice: Subject to any disclaimer, the term of this patent is extended or adjusted under 35 U.S.C. 154(b) by 539 days.

(21) Appl. No.: 12/489,916

(22) Filed: Jun. 23, 2009

(65) Prior Publication Data

US 2010/0324557 A1 Dec. 23, 2010

(51) Int. Cl.
*A61B 17/80* (2006.01)

(52) U.S. Cl. .......................................... 606/286

(58) Field of Classification Search .......... 606/246–279, 606/280–299, 300–331, 70, 71, 60
See application file for complete search history.

(56) References Cited

U.S. PATENT DOCUMENTS

| | | | |
|---|---|---|---|
| 3,940,945 A | 3/1976 | Härdmark et al. | |
| 5,545,164 A * | 8/1996 | Howland | 606/250 |
| 5,558,674 A * | 9/1996 | Heggeness et al. | 606/278 |
| 5,582,612 A * | 12/1996 | Lin | 606/250 |
| 6,146,382 A | 11/2000 | Hurlbert | |
| 6,524,315 B1 | 2/2003 | Selvitelli | |
| 6,547,790 B2 | 4/2003 | Harkey et al. | |
| 6,620,164 B2 | 9/2003 | Ueyama et al. | |
| 6,902,565 B2 * | 6/2005 | Berger et al. | 606/300 |
| 7,232,441 B2 * | 6/2007 | Altarac et al. | 606/250 |
| 7,303,563 B2 | 12/2007 | Poyner et al. | |
| 7,575,588 B2 * | 8/2009 | Barker et al. | 606/280 |
| 7,618,443 B2 * | 11/2009 | Abdou | 606/278 |
| 7,695,500 B2 * | 4/2010 | Markworth | 606/280 |
| 7,776,070 B2 * | 8/2010 | Null et al. | 606/252 |
| 7,901,433 B2 * | 3/2011 | Forton et al. | 606/250 |
| 2002/0143327 A1 | 10/2002 | Shluzas | |
| 2003/0004512 A1 | 1/2003 | Farris et al. | |
| 2003/0045878 A1 | 3/2003 | Petit | |
| 2003/0125741 A1 | 7/2003 | Biedermann et al. | |
| 2003/0153913 A1 | 8/2003 | Altarac et al. | |
| 2005/0283153 A1 | 12/2005 | Poyner et al. | |
| 2005/0288669 A1 | 12/2005 | Abdou | |
| 2006/0229610 A1 * | 10/2006 | Piehl | 606/61 |
| 2007/0049932 A1 | 3/2007 | Richelsoph et al. | |
| 2007/0118121 A1 | 5/2007 | Purcell et al. | |
| 2009/0018547 A1 | 1/2009 | Crews | |
| 2009/0270924 A1 * | 10/2009 | Wing et al. | 606/280 |

FOREIGN PATENT DOCUMENTS

EP    1 180 348 A2    2/2002

(Continued)

OTHER PUBLICATIONS

PCT International Search Report for International Application No. PCT/US2006/037385; Search Report Completed Feb. 5, 2007 and Mailed Feb. 19, 2007.

(Continued)

*Primary Examiner* — Kevin T Truong
*Assistant Examiner* — Christopher Beccia

(57) ABSTRACT

A bone plate for securing a spinal fixation element to bone includes a base portion having a top face, a rod receiving portion and a bone anchor receiving portion. The bone anchor receiving portion includes a plurality of angled holes for receiving bone screws. At least one of the screw holes is oriented at an acute angle relative to the top face of the plate.

16 Claims, 7 Drawing Sheets

FOREIGN PATENT DOCUMENTS

| | | |
|---|---|---|
| EP | 1 459 690 | 9/2004 |
| JP | 2002 102241 | 4/2002 |
| WO | WO 98/41160 | 9/1998 |
| WO | WO 98/41160 A | 9/1998 |
| WO | WO 2004/069038 | 8/2004 |
| WO | WO 2004/069038 A2 | 8/2004 |
| WO | WO 2007/041085 | 4/2007 |
| WO | WO 2007/146482 | 12/2007 |

OTHER PUBLICATIONS

U.S. Appl. No. 12/088,580, filed Aug. 13, 2008.
Japanese Office Action for application for JP 2008-533500, dated Mar. 24, 2011 with English Translation.
USPTO Final Office Action for U.S. Appl. No. 12/088,580 dated Jul. 30, 2012.

* cited by examiner

MINIMAL ACCESS OCCIPITAL PLATE

FIELD OF THE INVENTION

The present invention relates generally to apparatuses and methods for treating the cervical spine, and more particularly to an occipital bone plate that can be used when access and work space around the occiput bone are limited.

BACKGROUND OF THE INVENTION

Occipitocervical fixation may be accomplished by using a bone plate attached to the occiput bone on the posterior of the skull, in conjunction with spinal rods. In many cases, the bone plate is attached to the skull with bone screws. Drilling and tapping holes at the rear of the skull is a difficult procedure that requires a significant amount of force to penetrate the dense cortical bone. The process is further complicated by the angle of approach that is required for instruments. Because the plate is positioned in close proximity to the back of the neck, the working area around the plate location is extremely confined. Moreover, the orientation of the plate is such that the plate extends more or less normal to the axis of the cervical spine. Typical bone plates feature holes with axes that extend normally to the surface of the plate. In this arrangement, the axes of the screw holes are very close to the axis of the cervical spine. Consequently, the surgeon must position screw drivers, drills and taps right up against the cervical spine to maintain the proper trajectory while drilling and tapping the occiput bone, and driving bone screws through the plate.

Conventional screw drivers, drills and taps have relatively long shafts. To position these instruments so as to achieve the proper trajectories, the shafts must be positioned normal to the plate, right up against the cervical spine. Therefore, the surgeon must make a long incision along the axis of the cervical spine to make room to maneuver the instrument shafts. Large incisions are clearly undesirable because they are invasive, introduce greater risk of complications, and require long recovery times. Moreover, longer incisions are not always effective in providing sufficient clearance for instruments. Cervical deformities that obstruct the area around the occiput bone, for example, can make it impossible to position instrument shafts at the proper angle necessary to access the screws.

For the foregoing reasons, conventional occipitocervical fixation implants and techniques have many unresolved drawbacks.

SUMMARY OF THE INVENTION

The drawbacks of conventional occipitocervical fixation implants and techniques are resolved in many respects by bone plates and assemblies in accordance with the present invention. In a first aspect of the invention, a bone plate for securing a spinal fixation element to bone includes a base portion having a top face, a rod receiving portion and a bone anchor receiving portion. The rod receiving portion extends from the base portion, and includes a channel for receiving a spinal fixation element. The bone anchor receiving portion includes one or more raised projections projecting from the top face of the plate. Each projection forms a hole for receiving a bone anchor into the raised projection and through the base portion. Each hole has a hole axis extending at an acute angle with respect to the top face.

In a second aspect of the invention, a bone plate for securing a spinal fixation element to bone includes a base portion having a top face, a rod receiving portion for receiving a spinal fixation element, and a bone anchor receiving portion. The bone anchor receiving portion includes one or more angled screw holes. Each screw hole has a hole axis extending at an acute angle with respect to the top face. The axes of two or more holes converge toward one another as they extend away from the top face of the plate.

BRIEF DESCRIPTION OF THE DRAWINGS

The foregoing summary and the following detailed description will be better understood in conjunction with the drawing figures, of which.

DETAILED DESCRIPTION OF PREFERRED EMBODIMENTS OF THE INVENTION

Figure 1:
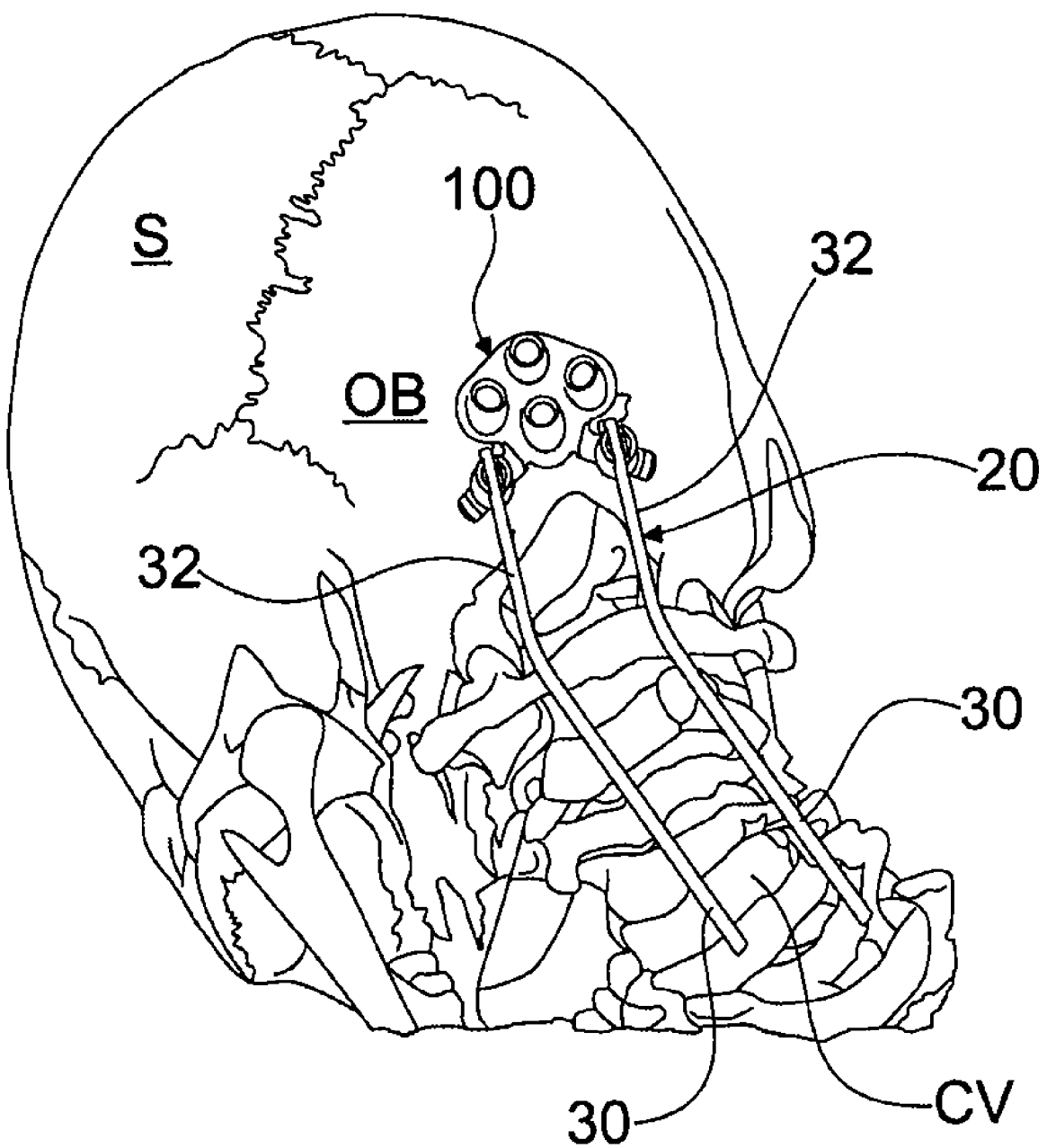
FIG. 1 is a perspective view of an occipitocervical fixation assembly in accordance with the invention, schematically shown as it would be positioned to stabilize a patient's cervical spine.

Although the invention is illustrated and described herein with reference to specific embodiments, the invention is not intended to be limited to the details shown. Rather, various modifications may be made in the details within the scope and range of equivalents of the claims and without departing from the invention.

Occipital bone plates in accordance with the present invention provide a mechanism for stabilizing the base of the skull and cervical spine, while allowing surgical instrumentation to be held away from the cervical spine. In addition, bone plates in accordance with the invention provide a mechanism that reduces the size of incisions. Moreover, bone plates in accordance with the invention provide a stronger engagement between the occiput bone and bone screws. These combined benefits are achieved by selective angulation of screw holes in the bone plate. By angulating screw holes with respect to a reference plane, such as the plate's base portion, the screw holes can be tapped and drilled, and bone screws can be inserted and driven into the proper depth in the bone, with sufficient work space and clearance. Bone plates in accordance with the invention can be used with conventional drills, taps and other instruments with elongated shafts. This avoids the need for special instruments, like drills with flexible shafts, that are shaped and designed to apply force from difficult approach angles. Flexible drills are difficult to use, because the surgeon cannot easily apply force behind the flexible drill shaft in the drilling direction to penetrate the dense cortical bone.

In preferred embodiments, the bone plate generally includes a base portion having a top face, a rod receiving portion and a bone anchor receiving portion. The rod receiving portion connects to one or more spinal fixation elements, such as spinal rods implanted over the cervical spine. The bone anchor receiving portion includes a number of holes or apertures designed to receive and securely hold bone screws. The holes are formed in raised projections that project from the top face of the base portion, and each hole has a hole axis that controls the orientation of the bone screw to be received in that hole.

Each raised projection is designed to orient the hole axis of the corresponding screw hole in a predetermined angle. The angular orientation of each hole axis allows the surgeon to position instruments away from the patient's spine. More specifically, the angular orientation of the holes allow elongated shafts of drills, taps and drivers to access the plate at acute angles relative to the axis of the cervical spine, thereby positioning the instrument's body out and away from the patient's spine. As explained in more detail below, preferred embodiments of the invention have hole angulations that collectively minimize the incision through which instruments access the plate. This can be achieved by orienting two or more hole axes in a converging arrangement, so that the axes intersect at a point above the plate.

The angular orientation of the screw hole axes may be measured with respect to any reference plane, such as an imaginary plane normal to the occipital bone at a point where the plate contacts the bone. For example, using the perimeter of the plate section that contacts the bone, the centroid of the plate's footprint contacting the bone may be selected as the point through which to define the reference plane, which may be tangential or parallel to the bone surface at that point. Alternatively, the reference plane may be a plane that passes through the top face of the plate, assuming the top face is flat or has flat sections. The top face of the plate need not be flat, however, as various curvatures and contours may be incorporated on the plate's top surface in accordance with the invention. Where the top face is curved, a reference plane that is tangential to a point on the top face may be used to define the angular orientation of a hole axis. Accordingly, angular orientations of screw hole axes may be measured based on various reference planes that include but are not limited to planes that coincide with or are tangential to the top face of the plate, or planes that coincide with or are tangential to a section of occipital bone.

Referring now to FIG. 1, a fixation system 20 is shown in accordance with one exemplary embodiment of the invention, illustrated schematically with portions of a skull S and cervical vertebrae CV. Fixation system 20 includes a pair of spinal fixation rods 30 that are attached to cervical vertebrae in the spine. Each rod 30 has a curved or bent end 32 that is secured to the base of the skull, thereby creating a fixation member that stabilizes the cervical vertebrae and skull in a fixed position. Rod ends 32 are secured to the base of the skull by a bone plate 100 that is attached to the occiput bone OB of the skull.

Various directional terms are used herein to describe relative positions and directions. Unless otherwise specified, the term "posterior" refers to a position or direction toward the patient's back side. Moreover, unless otherwise specified, the term "superior" refers to features that are positioned toward the patient's skull after implantation, and the term "inferior" refers to features that are positioned toward the patient's feet after implantation, relative to a corresponding superior feature. Furthermore, unless otherwise specified, the term "lateral" refers to features that would be positioned toward the patient's left side or right side after implantation, relative to the patient's spine.

Figure 2:
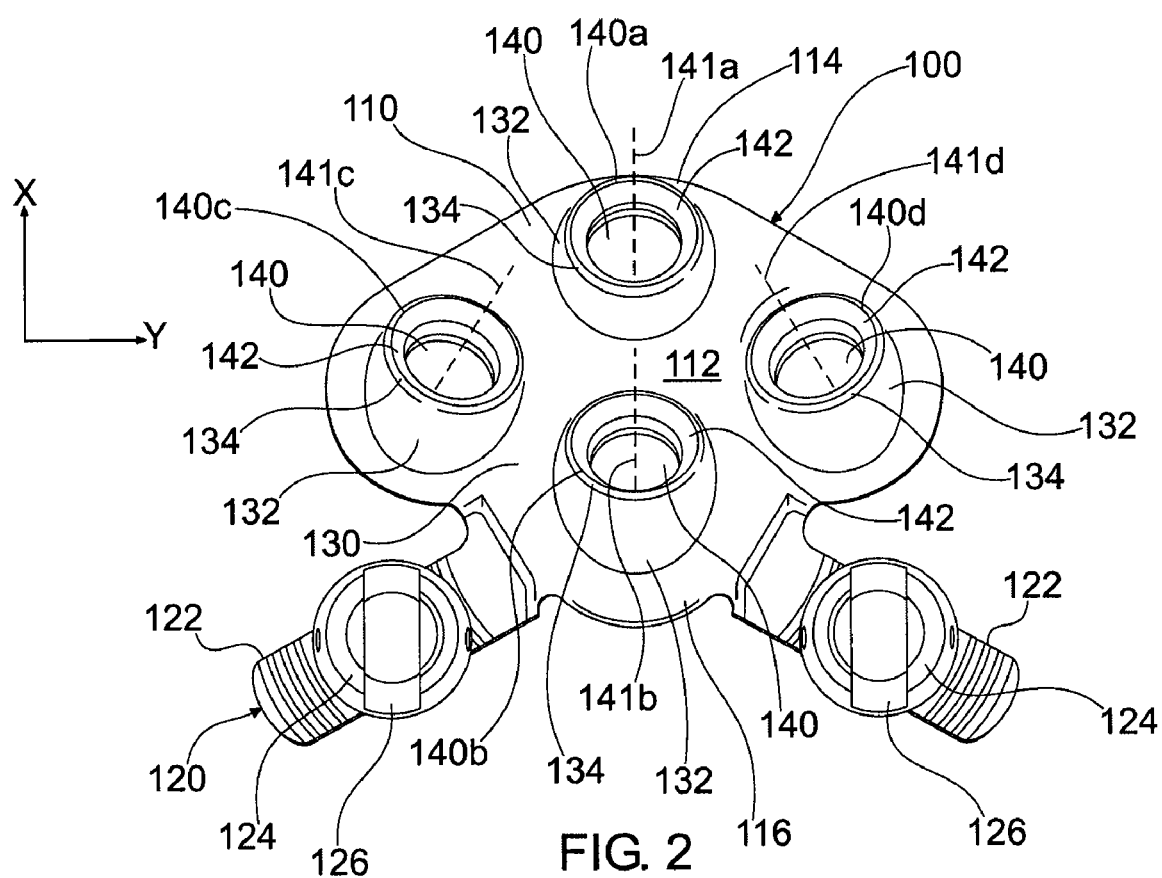
FIG. 2 is a front view of an exemplary occiput bone plate with a pair of receiver elements for receiving spinal fixation elements.

Referring now to FIG. 2, bone plate 100 includes a base portion 110 having a flat top face 112, a superior end 114 and an inferior end 116. A rod receiving portion 120 extends from inferior end 116. Rod receiving portion 120 includes a pair of arms 122, with each arm having a front face 123 and a generally cylindrical receiver body 124 extending from the front face. Each receiver body 124 includes a U-shaped channel 126 adapted to receive one of the rod ends 32. Each rod end 32 bends in a posterior direction into alignment with one of the U-shaped channels 126 on the receiver bodies 124 on bone plate 100. Rod ends 32 can be secured in receiver bodies 124 by any type of fastener, such as set screws having external threads that engage threading in the U-shaped channels 126.

Bone plates in accordance with the invention include a bone anchor receiving portion designed to receive bone screws at selected angles, as noted above. The selected angles allow instruments to be tilted away from the cervical spine, so that the surgeon only needs to position a small part of the shaft's distal end near the cervical spine. Tilting or angling the instrument away from the axis of the cervical spine provides more working room for the surgeon.

In preferred embodiments, the hole angles not only to allow tilting of instrument shafts away from the spine, but also cooperate with one another to minimize the required size of the incision. For example, screw holes may be angled so that their axes converge toward one another and intersect on or near a point of incision on the patient's skin. In this arrangement, the shaft of a drill (or other instrument) can be inserted through one small incision and pivoted within that incision to access each screw hole. The surgeon is able to direct the tip of the instrument shaft to each screw hole through the same small incision, without the need to make one large incision or multiple small incisions to access each screw hole location. It is preferable that at least two of the screw hole axes converge toward one another, and more preferable that all the screw hole axes converge toward one another so as to intersect at one or more points above the plate location. Even more preferably, all of the screw holes in the plate converge toward one another and intersect at a single point which, after the plate is implanted, coincides with a single point of incision on the patient's skin.

The screw hole axes may be angled in a number of ways to guide the trajectory of instruments and bone screws. For example, the screw hole angles may be provided by oblique passages that extend through the plate at desired angles. Alternatively, the screw hole angles can be provided by oblique passages in combination with raised protruberances, such as raised projections or bosses, that extend out from the top face of the plate. The protuberances provide a more convenient way to manufacture the angled holes. Referring to FIG. 2, for example, bone plate 100 includes a bone anchor receiving portion 130 with four raised projections or bosses 132. Projections 132, which are formed when the plate is stamped, are rounded hubs with relatively flat end faces 134. Each end face 134 has a screw hole 140 for receiving a bone screw or other anchoring element through the plate.

Screw holes 140 may be formed through end faces 134 by punching the holes through the end faces. Each end face 134 is planar, or more or less follows a plane. The plane of each end face preferably extends normal to the screw hole axis that passes through end face. Screw holes in accordance with the invention may include a variety of seat configurations for receiving the heads of bone screws. In FIG. 2, screw holes 140 contain conical shaped seat surfaces 142 for receiving monoaxial screws.

Bone plates in accordance with the invention may have a number of different hole sizes, configurations and arrangements. As discussed above, and as will be explained in more detail below, the hole sizes, hole configurations and hole arrangements can be selected in different combinations to achieve a number of benefits. One hole arrangement in accordance with the invention, shown in FIG. 2, features four screw holes 140 arranged in a diamond-shaped configuration. Holes 140 include a superior hole 140a, an inferior hole 140b, a first lateral hole 140c and a second lateral hole 140d. Plates in accordance with the invention may have fewer holes or more holes, and need not be limited to four.

Figure 3:
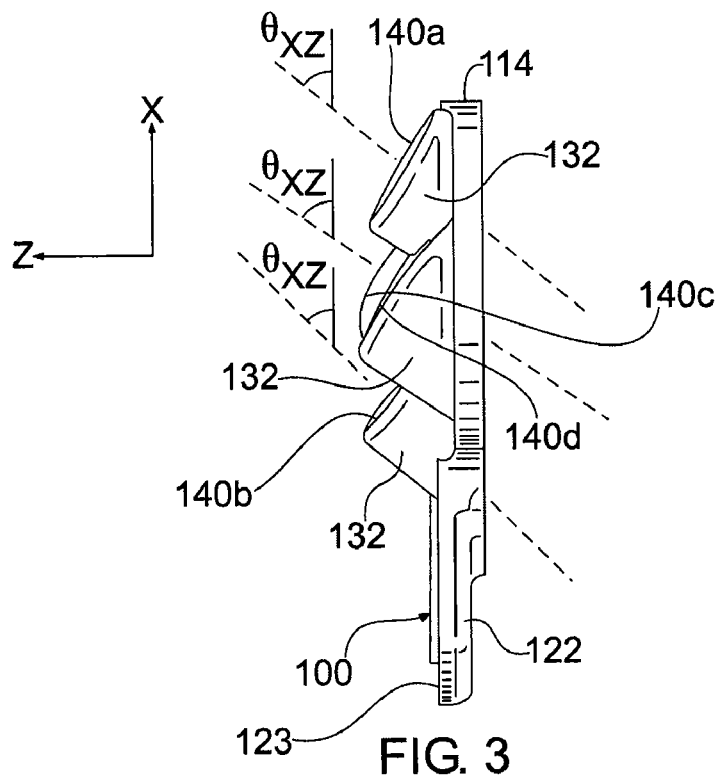
FIG. 3 is a side view of the occiput bone plate of FIG. 2, with the rod receiver elements removed.
Figure 5:
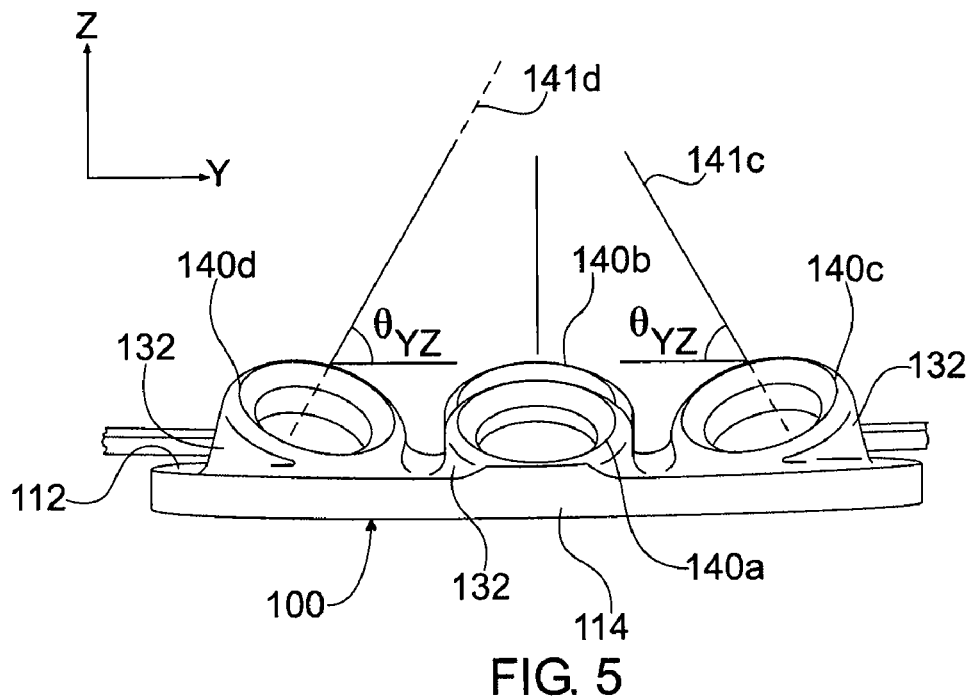
FIG. 5 is a top view of the occiput bone plate of FIG. 2.

Holes 140a-140d have longitudinal axes 141a-141d, respectively, that extend through the plate and define the final orientations of the screws that are inserted through the screw holes. Referring now to FIGS. 2, 3 and 5, hole axes 141a-141d form acute angles with top face 112 of plate 100 and converge toward one another as they extend away from the top face as shown. For purposes herein, the orientations of hole axes 141a-141d are described in terms of angles based on three reference axes, X, Y and Z shown in the drawings, and imaginary planes between the axes. The Figures show three planes of reference, which include the X-Y plane coinciding with top face 112 of plate 100 (see FIG. 2), the Y-Z plane that extends normal to top face 112 (see FIG. 5), and the X-Z plane that extends perpendicularly to the X-Y and Y-Z planes (FIG. 3).

Each hole axis is characterized by an angle $\Theta_{XZ}$ relative to top face 112 that extends in a plane parallel to the X-Z plane. Examples of these angles are shown in FIG. 3. Each hole axis also has an angle $\Theta_{YZ}$, which is the angle relative to top face 112 extending in a plane parallel to the Y-Z plane. Examples of these angles are shown in FIG. 5.

Referring now to FIG. 3, a side view of bone plate 100 is shown. From this side view, it is apparent that all four projections 132 are oriented with their end faces and screw holes angled toward superior end 114 of bone plate 100. That is, the axes of screw holes 140a-140d extend at acute angles $\Theta_{XZ}$ with respect to top face 112. The axis of the superior screw hole 140a preferably forms an angle $\Theta_{XZ}$ of between about 55 and about 65 degrees, more preferably between about 58 degrees and about 62 degrees, and even more preferably at an angle of about 60 degrees. The axes of the first and second lateral holes 140c and 140d preferably form an angle $\Theta_{XZ}$ of between about 52 and about 62 degrees, more preferably between about 55 degrees and about 59 degrees, and even more preferably at an angle of about 57 degrees. Lastly, the axis of inferior screw hole 140b forms an angle $\Theta_{XZ}$ of between about 47 degrees and about 57 degrees, more preferably between about 50 degrees and about 54 degrees, and even more preferably at an angle of about 52 degrees.

Figure 4:
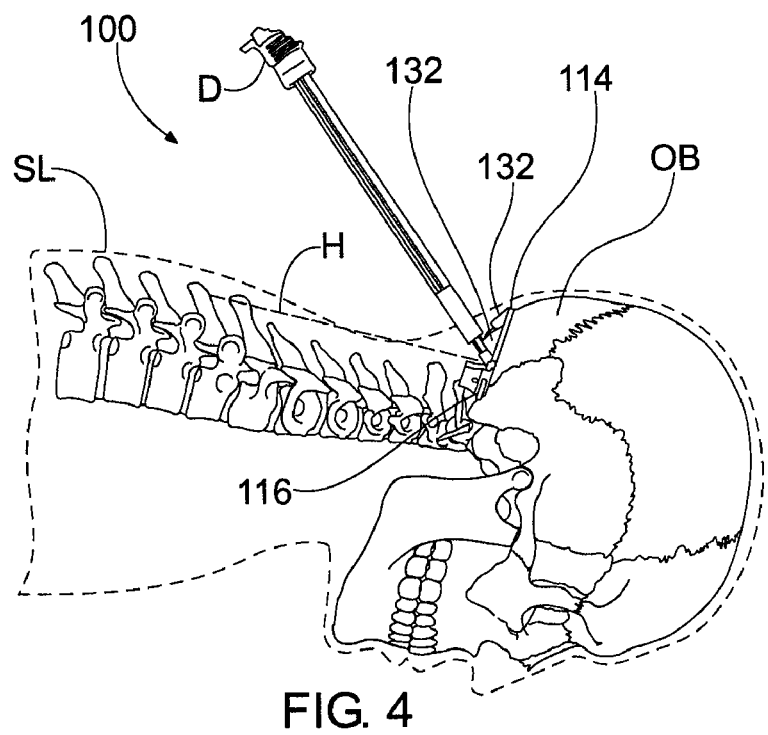
FIG. 4 is a side view of the occiput bone plate of FIG. 2, shown in a schematic illustration of a technique for attaching the plate to the occiput bone of a patient's skull in accordance with the invention.

The hole orientations described above result in screw holes that are angled upwardly or toward superior end 114 of plate 100 as the holes extend toward the top face. By angling screw holes toward the superior end of a bone plate, instruments can engage the plate easily using an "angled approach." FIG. 4 schematically illustrates a benefit of using an angled approach provided by the invention. In FIG. 4, bone plate 100 is in the process of being secured to a patient's occiput bone OB. The surface of the patient's skin is schematically illustrated by the skin line "SL". A screw driver D approaches a screw hole in plate 100 at a relatively small angle with respect to the plate, to drive a bone screw through the plate. The orientations of projections 132 and the screw hole axes allow screw driver D to approach the plate from a position that is offset away from the spine (i.e. posteriorly to the cervical spine axis). As such, screw driver D is advanced toward the screw holes from a position that is mostly above skin line SL. Only a very small section of screw driver D at the screw driver's distal end must be positioned near skin line SL. Accordingly, plate 100 only requires a very small incision in proximity to the plate to provide access for long screw drivers and other instrumentation.

Plates that feature hole axes oriented normally to the mounting surface of the occiput bone surface do not permit conventional bone screws and long shafted instruments from approaching the plate in an angled approach. Instead, the shafts of instruments must be held normal to the plate, or substantially normal to the plate, as represented by line "H" in FIG. 4. In such a position, there is little or no clearance around the shaft, making it difficult to manipulate the instrument and advance bone screws at the proper trajectories into the plate holes. In some cases, the entire shaft of screw driver D must be positioned inside the patient beneath skin line SL, more or less adjacent to the axis of the cervical spine. To provide sufficient space around the shaft, a long incision must be made above the cervical spine to receive the entire length of screw driver D and allow the screw driver end to approach the screw holes from a direction normal to plate P. Large incisions are undesirable, as noted above, because they are very invasive, increase risks of complications during and after surgery, and lengthen recovery time, as compared to procedures using smaller incisions. Moreover, placing an instrument inside an incision above the cervical spine is not always possible. Spinal deformities and other factors can create obstructions that prevent a long instrument from being placed in the incision and advanced in a direction normal to the plate.

Figure 10:
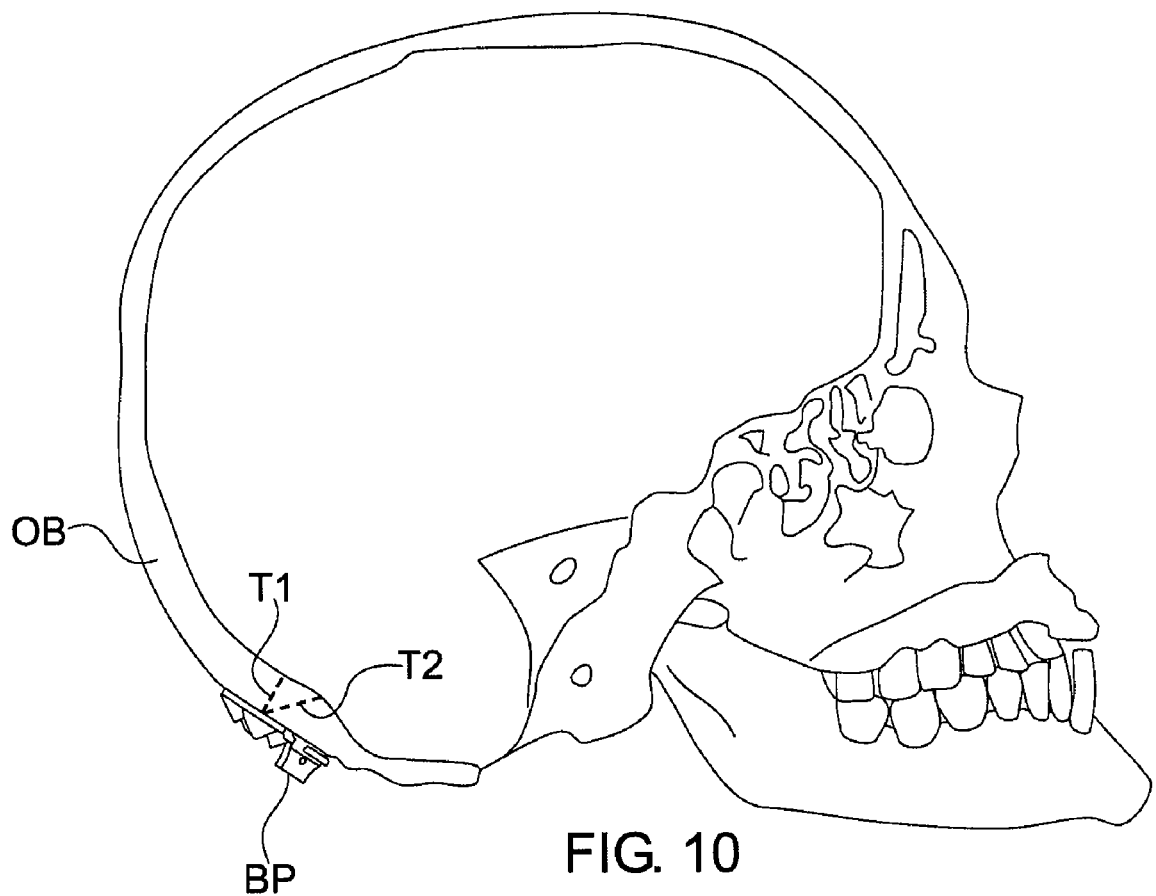
FIG. 10 is a cross-sectional view of a skull illustrating different screw trajectories through the occiput bone.

Another advantage of angling the screw holes toward the superior end of bone plate 100 is improved contact between the bone screws and the occiput bone. The occiput bone is a saucer shaped bone which varies in thickness along its length. FIG. 10 shows a cross-section of a skull, showing the thickness variation along the length of occiput bone OB. A bone plate BP is attached to occiput bone OB, and two possible screw trajectories $T_1$ and $T_2$ are shown. Screws that are advanced through plate BP along an axis normal to the plate would follow trajectory $T_1$. Screws that are advanced through bone plate BP at the same point, but using an angled approach in accordance with the invention, would follow trajectory $T_2$. In trajectory $T_2$, the screw shanks extend through a longer length of bone than in trajectory $T_1$. That is, the orientation of trajectory $T_2$ traverses a greater length of bone than trajectory $T_1$. Therefore, trajectory $T_2$ provides a greater degree of bone penetration than trajectory $T_1$, allowing for greater screw purchase in the bone, and accommodating longer bone screws, if desired.

Preferred plates in accordance with the invention provide hole axes that are angled toward the superior end of the plate, as noted above. The holes axes may be parallel to one another. In more preferred embodiments, however, the holes axes converge toward one another as they extend away from the top plate, and consequently diverge away from one another as they extend into the bone. Referring to FIG. 5, a top view of bone plate 100 is shown, looking into superior end 114 of the plate. Projections 132 associated with first and second lateral holes 140c and 140d are oriented with their end faces toward the center of bone plate 100. The axes of screw holes 140c and 140d extend at acute angles $\Theta_{YZ}$ with respect to top face 112. In contrast, the axes of superior screw hole 140a and inferior screw hole 140b are not angled in the Y-Z direction, with their respective angles $\Theta_{YZ}$ being right angles. The axes of first and second lateral holes 140c and 140d preferably extend at angles $\Theta_{YZ}$ of between about 73 and about 83 degrees, more preferably between about 76 degrees and about 80 degrees, and even more preferably at an angle of about 78 degrees.

Figure 6:
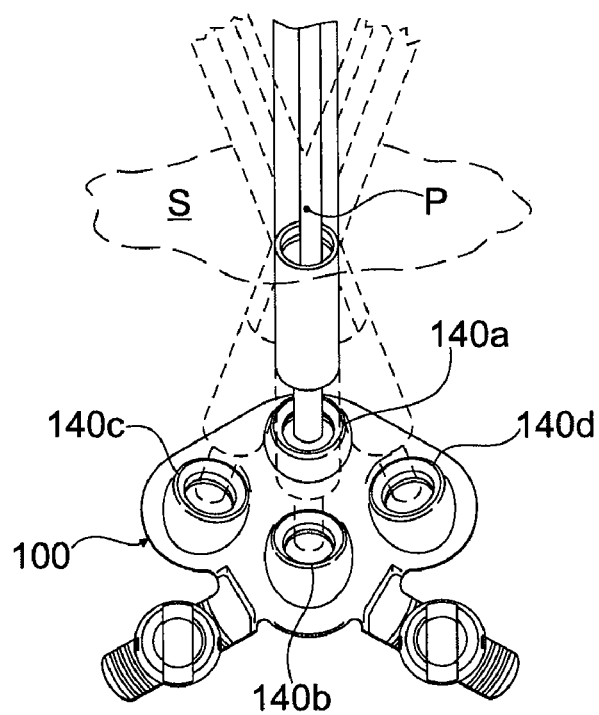
FIG. 6 is a front view of the occiput bone plate of FIG. 2, shown being engaged by an instrument in four possible positions.

Based on the foregoing hole angles, hole axes 141a-141d converge toward one another as they extend outwardly from top face of plate 112 (i.e. they converge as they extend in the posterior direction away from the skull when the plate is implanted), and diverge from one another as they extend in the opposite direction. This has multiple benefits. By converging in the posterior direction, the axes allow the surgeon to minimize the size of the incision needed to access the plate. The intersecting axes allow instruments to access the plate through very small incisions, or even a single incision, depending on where they intersect. In a preferred embodiment, hole axes 141a-141d are oriented so as to converge at a single point on the patient's skin, which corresponds to a single entry point for an instrument. This configuration allows an instrument to access all of the screw holes while extending from a single entry point through the patient's skin, as illustrated schematically in FIG. 6. FIG. 6 shows screw driver D inserted through a single entry point P of a patient's skin S, in four possible positions (with three positions shown in phantom lines for clarity). Screw driver D accesses a different screw hole in each of the illustrated positions. The screw hole axes intersect at point P. Consequently, the shaft of the screw driver intersects point P in each of the four positions. As such, a single small incision at entry point P will accommodate the screw driver D and allow it to access each of the four screw holes.

Figure 7:
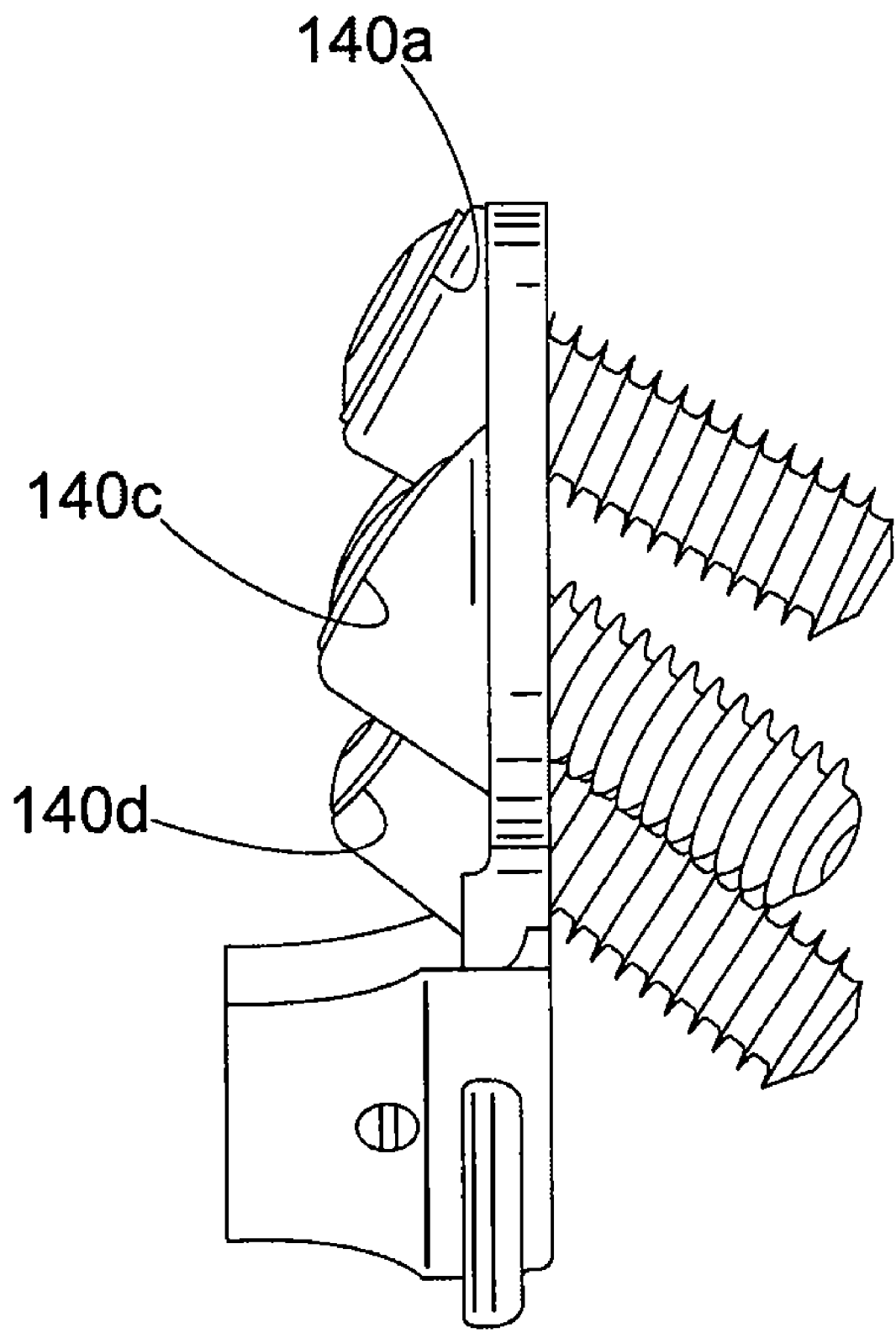
FIG. 7 is a side view of the occiput bone plate of FIG. 2, shown with a plurality of bone screws inserted through the plate.

Hole axes 141a-141d diverge away from one another as they extend in the bone, as noted above. This has the additional benefit of improving the anchorage of the plate. FIG. 7 shows one possible arrangement in which screws are inserted through screw holes 140a-140d. The diverging hole axes allow the shanks of the bone screws to spread apart from one another in the bone, providing a wider support structure. Because the screw axes are non-parallel, the plate is reinforced against pull-out in multiple directions.

Figure 8:
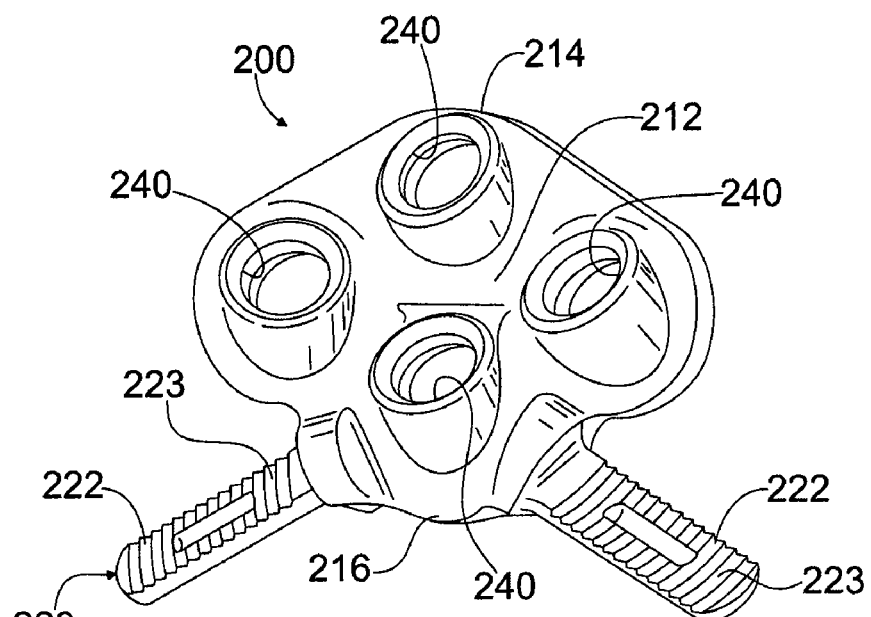
FIG. 8 is a perspective view of a bone plate in accordance with an alternative embodiment of the invention.
Figure 9:
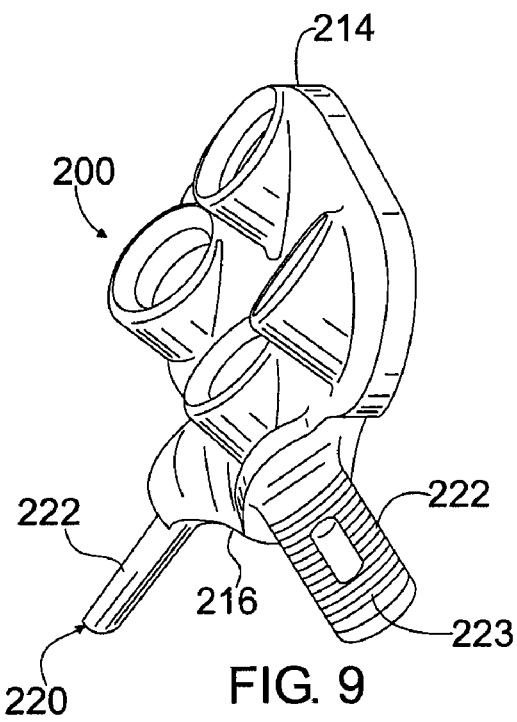
FIG. 9 is another perspective view of the bone plate of FIG. 8.

Referring now to FIGS. 8 and 9, a bone plate 200 is shown in accordance with an alternative embodiment of the invention. Bone plate 200 is similar in many respects to bone plate 100 but features a modified rod receiving portion 220. Plate 200 includes a superior end 214, inferior end 216, flat top face 212 and four angled screw holes 240 that project outwardly from the top face. Rod receiving portion 220 includes a pair of arms 222 with front faces 223 that are tilted upwardly toward the superior end 214 of plate 200. This is in contrast to arms 122 on plate 100, which have faces 123 oriented more or less parallel to top face 112, as seen in FIG. 3. The tilted faces 223 on plate 200 allow rod receivers to be mounted on arms 222 so that the openings in the rod receivers are angled upwardly, similar to screw holes 240. FIGS. 8 and 9 are shown without rod receivers on arms 222 so that the entire faces 223 can be seen. When plate 200 is attached to the skull, the tilted arms 222 support rod receivers with their openings angled upwardly so that instruments can access the rod receivers with the same angled approach used to access the screw holes.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A bone plate for securing a spinal fixation element to bone, the bone plate comprising:
   a base portion having a top face;
   a rod receiving portion extending from the base portion, the rod receiving portion including a channel for receiving a spinal fixation element; and
   a bone anchor receiving portion comprising a plurality of raised projections, each raised projection projecting from the top face of the plate and forming a hole for receiving a bone anchor into the raised projection and through the base portion, each hole having a hole axis extending at an acute angle with respect to the top face, wherein the bone anchor receiving portion is characterized by an X-Y plane, a Y-Z plane and an X-Z plane, with at least one hole axis oriented at an acute angle with respect to the top face in a plane parallel to one of the X-Y plane, Y-Z plane and X-Z plane, and another hole axis oriented at an acute angle with respect to the top face in a plane parallel to another of the X-Y plane, Y-Z plane and X-Z plane.

2. The bone plate of claim 1, wherein the axes of all of the holes converge at a single point above the top face of the plate.

3. The bone plate of claim 1, wherein the holes comprise a superior hole, an inferior hole, a first lateral hole and a second lateral hole.

4. The bone plate of claim 3 wherein the axis of the superior hole extends at an acute angle $\Theta_{XZ}$ relative to the top face, and the inferior hole extends at an acute angle $\theta_{XZ}$ relative to the top face, wherein angle $\Theta_{XZ}$ for the superior hole is greater than $\Theta_{XZ}$ for the inferior hole.

5. The bone plate of claim 4, wherein angle $\Theta_{XZ}$ for the superior hole is between about 55 degrees and about 65 degrees, and angle $\Theta_{XZ}$ for the inferior hole is between about 47 degrees and about 57 degrees.

6. The bone plate of claim 3, wherein the axis of the first lateral hole extends at an acute angle $\Theta_{XZ}$ relative to the top face and an angle $\Theta_{YZ}$ relative to the top face, wherein angle $\Theta_{YZ}$ for the first lateral hole is greater than angle $\Theta_{XZ}$ for the first lateral hole.

7. The bone plate of claim 6, wherein the axis of the second lateral hole extends at an acute angle $\Theta_{XZ}$ relative to the top face and an angle $\Theta_{YZ}$ relative to the top face, wherein angle $\Theta_{YZ}$ for the second lateral hole is greater than angle $\Theta_{XZ}$ for the second lateral hole.

8. The bone plate of claim 7, wherein angles $\Theta_{XZ}$ for the first and second lateral holes are between about 52 degrees and about 62 degrees, and angles $\Theta_{YZ}$ for the first and second lateral holes are between about between about 73 degrees and about 83 degrees, the first and second lateral holes being symmetrically arranged on the top face of the plate.

9. A bone plate for securing a spinal fixation element to bone, the bone plate comprising:
   a base portion having a top face;
   a rod receiving portion for receiving a spinal fixation element; and
   a bone anchor receiving portion comprising a plurality of raised projections, each raised projection projecting from the top face of the plate and forming a hole for receiving a bone anchor into the raised projection and through the base portion, each hole having a hole axis extending at an acute angle with respect to the top face, the axes of the holes converging toward one another as they extend away from the top face of the plate, wherein the bone anchor receiving portion is characterized by an X-Y plane, a Y-Z plane and an X-Z plane, with at least one hole axis oriented at an acute angle with respect to the top face in a plane parallel to one of the X-Y plane, Y-Z plane and X-Z plane, and another hole axis oriented at an acute angle with respect to the top face in a plane parallel to another of the X-Y plane, Y-Z plane and X-Z plane.

10. The bone plate of claim 9, wherein the axes of all of the holes converge at a single point above the top face of the plate.

11. The bone plate of claim 10, wherein the holes comprise a superior hole, an inferior hole, a first lateral hole and a second lateral hole.

12. The bone plate of claim 11 wherein the axis of the superior hole extends at an acute angle $\Theta_{XZ}$ relative to the top face, and the inferior hole extends at an acute angle $\Theta_{XZ}$ relative to the top face, wherein angle $\Theta_{XZ}$ for the superior hole is greater than $\Theta_{XZ}$ for the inferior hole.

13. The bone plate of claim 12, wherein angle $\Theta_{XZ}$ for the superior hole is between about 55 degrees and about 65 degrees, and angle $\Theta_{XZ}$ for the inferior hole is between about 47 degrees and about 57 degrees.

14. The bone plate of claim 11, wherein the axis of the first lateral hole extends at an acute angle $\Theta_{XZ}$ relative to the top face and an angle $\Theta_{YZ}$ relative to the top face, wherein angle $\Theta_{YZ}$ for the first lateral hole is greater than angle $\Theta_{XZ}$ for the first lateral hole.

15. The bone plate of claim 14, wherein the axis of the second lateral hole extends at an acute angle $\Theta_{XZ}$ relative to the top face and an angle $\Theta_{YZ}$ relative to the top face, wherein angle $\Theta_{YZ}$ for the second lateral hole is greater than angle $\Theta_{XZ}$ for the second lateral hole.

16. The bone plate of claim 15, wherein angles $\Theta_{XZ}$ for the first and second lateral holes are between about 52 degrees and about 62 degrees, and angles $\Theta_{YZ}$ for the first and second lateral holes are between about between about 73 degrees and about 83 degrees.

* * * * *

UNITED STATES PATENT AND TRADEMARK OFFICE
CERTIFICATE OF CORRECTION

PATENT NO. : 8,348,981 B2
APPLICATION NO. : 12/489916
DATED : January 8, 2013
INVENTOR(S) : Naveed Cheema et al.

It is certified that error appears in the above-identified patent and that said Letters Patent is hereby corrected as shown below:

At FIELD (73) on the title page "Aesculap Implany Systems, LLC" should read
-- Aesculap Implant Systems, LLC --

Signed and Sealed this
Ninth Day of April, 2013

Teresa Stanek Rea
*Acting Director of the United States Patent and Trademark Office*